(12) United States Patent
Schneider

(10) Patent No.: US 12,179,437 B2
(45) Date of Patent: Dec. 31, 2024

(54) METHOD AND APPARATUS FOR ASSEMBLING APERTURED ELASTIC LAMINATES

(71) Applicant: The Procter & Gamble Company, Cincinnati, OH (US)

(72) Inventor: Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 532 days.

(21) Appl. No.: 17/541,585

(22) Filed: Dec. 3, 2021

(65) Prior Publication Data

US 2022/0088889 A1  Mar. 24, 2022

Related U.S. Application Data

(62) Division of application No. 16/903,501, filed on Jun. 17, 2020, now Pat. No. 11,220,065.

(Continued)

(51) Int. Cl.
*A61F 13/15* (2006.01)
*A61F 13/49* (2006.01)
(Continued)

(52) U.S. Cl.
CPC ...... *B29C 66/83411* (2013.01); *B29C 65/086* (2013.01); *B29C 65/74* (2013.01);
(Continued)

(58) Field of Classification Search
CPC . B29C 66/83411; B29C 65/086; B29C 65/74; B29C 65/7894; B29C 66/45;
(Continued)

(56) References Cited

U.S. PATENT DOCUMENTS 3,113,225 A   12/1963   Claus
3,562,041 A   2/1971   Robertson
(Continued)

FOREIGN PATENT DOCUMENTS

WO       9849249 A1    11/1998
WO    2015041928 A1     3/2015

OTHER PUBLICATIONS

All Office Actions; U.S. Appl. No. 16/903,501, filed Jun. 17, 2020.
(Continued)

*Primary Examiner* — Benjamin J Klein
*Assistant Examiner* — Gabriella E Burnette
(74) *Attorney, Agent, or Firm* — Charles R. Matson

(57) ABSTRACT

The present disclosure relates to methods for making apertured elastic laminates that may be used as components of absorbent articles. The methods and apparatuses may be close coupled such that materials may advance directly between aperturing and bonding operations. Such close coupling of devices may help to more precisely control the positions of the apertures in substrates relative to positions of apertures opposing substrates and/or bonds in the assembled laminate. The methods and apparatuses herein may also provide the ability to orient protrusions or protuberances in the substrates created by the aperturing process so as to extend inward and away from both outer surfaces of the assembled laminate. In turn, the assembly processes may be conducted so as to help mitigate reductions in softness that might otherwise result from the aperturing process in the assembled laminate.

5 Claims, 14 Drawing Sheets

Related U.S. Application Data

(60) Provisional application No. 62/874,600, filed on Jul. 16, 2019.

(51) Int. Cl.
| | | |
|---|---|---|
| *B29C 65/00* | (2006.01) | |
| *B29C 65/08* | (2006.01) | |
| *B29C 65/74* | (2006.01) | |
| *B29C 65/78* | (2006.01) | |
| *B29L 31/48* | (2006.01) | |

(52) U.S. Cl.
CPC .......... *B29C 65/7894* (2013.01); *B29C 66/45* (2013.01); *B29C 66/7392* (2013.01); *A61F 13/15593* (2013.01); *A61F 13/15699* (2013.01); *A61F 13/15707* (2013.01); *A61F 13/15723* (2013.01); *A61F 13/49* (2013.01); *A61F 13/49009* (2013.01); *A61F 2013/49025* (2013.01); *B29L 2031/4878* (2013.01)

(58) Field of Classification Search
CPC .......... B29C 66/7392; A61F 13/15593; A61F 13/15699; A61F 13/15707; A61F 13/15723; A61F 13/49; A61F 13/49009; A61F 2013/49025; A61F 13/512; A61F 13/5146; B29L 2031/4878
See application file for complete search history.

(56) References Cited

U.S. PATENT DOCUMENTS

| | | |
|---|---|---|
| 3,733,238 A | 5/1973 | Long |
| 3,860,003 A | 1/1975 | Buell |
| 4,610,678 A | 9/1986 | Weisman |
| 4,673,402 A | 6/1987 | Weisman |
| 4,695,278 A | 9/1987 | Lawson |
| 4,704,115 A | 11/1987 | Buell |
| 4,761,450 A | 8/1988 | Lakshmanan |
| 4,795,454 A | 1/1989 | Dragoo |
| 4,834,735 A | 5/1989 | Alemany |
| 4,854,984 A | 8/1989 | Ball |
| 4,886,632 A | 12/1989 | Van |
| 4,888,231 A | 12/1989 | Angstadt |
| 4,909,803 A | 3/1990 | Aziz |
| 4,940,464 A | 7/1990 | Van Gompel et al. |
| 5,092,861 A | 3/1992 | Nomura |
| 5,110,403 A | 5/1992 | Ehlert |
| 5,167,897 A | 12/1992 | Weber et al. |
| 5,246,433 A | 9/1993 | Hasse |
| 5,360,420 A | 11/1994 | Cook et al. |
| 5,562,646 A | 10/1996 | Goldman et al. |
| 5,569,234 A | 10/1996 | Buell |
| 5,599,335 A | 2/1997 | Goldman et al. |
| 5,628,097 A | 5/1997 | Benson |
| 5,643,588 A | 7/1997 | Roe |
| 5,669,894 A | 9/1997 | Goldman et al. |
| 5,674,216 A | 10/1997 | Buell et al. |
| 5,702,551 A | 12/1997 | Huber et al. |
| 5,897,545 A | 4/1999 | Kline |
| 5,916,661 A | 6/1999 | Benson |
| 5,957,908 A | 9/1999 | Kline |
| 5,968,025 A | 10/1999 | Roe |
| 6,036,796 A | 3/2000 | Halbert |
| 6,107,537 A | 8/2000 | Elder |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson |
| 6,153,209 A | 11/2000 | Vega et al. |
| 6,248,195 B1 | 6/2001 | Schmitz |
| 6,291,039 B1 | 9/2001 | Combe |
| 6,410,129 B2 | 6/2002 | Zhang |
| 6,426,444 B2 | 7/2002 | Roe et al. |
| 6,508,641 B1 | 1/2003 | Kubik |
| 6,545,197 B1 | 4/2003 | Muller et al. |
| 6,575,949 B1 | 6/2003 | Waksmundzki et al. |
| 6,586,652 B1 | 7/2003 | Warner et al. |
| 6,617,016 B2 | 9/2003 | Zhang et al. |
| 6,627,787 B1 | 9/2003 | Roe et al. |
| 6,645,330 B2 | 11/2003 | Pargass |
| 6,676,054 B2 | 1/2004 | Heaney |
| 6,790,798 B1 | 9/2004 | Suzuki et al. |
| 6,825,393 B2 | 11/2004 | Roe et al. |
| 6,861,571 B1 | 3/2005 | Roe et al. |
| 7,569,039 B2 | 8/2009 | Matsuda |
| 7,878,447 B2 | 2/2011 | Hartzheim |
| 7,905,446 B2 | 3/2011 | Hartzheim |
| 8,186,296 B2 | 5/2012 | Brown et al. |
| 8,778,127 B2 | 7/2014 | Schneider et al. |
| 9,005,392 B2 | 4/2015 | Schneider |
| 9,156,648 B2 | 10/2015 | Yamamoto |
| 9,248,054 B2 | 2/2016 | Brown et al. |
| 9,265,672 B2 | 2/2016 | Brown et al. |
| 9,295,590 B2 | 3/2016 | Brown et al. |
| 9,730,839 B2 | 8/2017 | Brown |
| 9,962,297 B2 | 5/2018 | Eckstein |
| 10,052,237 B2 | 8/2018 | Galie |
| 2002/0016122 A1* | 2/2002 | Curro .................. A61Q 19/00 428/103 |
| 2003/0233082 A1 | 12/2003 | Kline |
| 2004/0097895 A1 | 5/2004 | Busam et al. |
| 2004/0158212 A1 | 8/2004 | Ponomarenko et al. |
| 2005/0107764 A1 | 5/2005 | Matsuda et al. |
| 2009/0312730 A1 | 12/2009 | LaVon et al. |
| 2012/0061015 A1 | 3/2012 | Lavon et al. |
| 2012/0061016 A1 | 3/2012 | Lavon et al. |
| 2012/0178333 A1 | 7/2012 | Fowler |
| 2013/0072887 A1 | 3/2013 | Lavon |
| 2013/0211356 A1 | 8/2013 | Nishikawa et al. |
| 2013/0255861 A1 | 10/2013 | Schneider |
| 2013/0255862 A1 | 10/2013 | Schneider et al. |
| 2013/0255863 A1 | 10/2013 | Lavon et al. |
| 2013/0255864 A1 | 10/2013 | Schneider et al. |
| 2013/0255865 A1 | 10/2013 | Brown et al. |
| 2013/0306226 A1 | 11/2013 | Zink |
| 2014/0148773 A1 | 5/2014 | Brown |
| 2016/0166443 A1 | 6/2016 | Arora et al. |
| 2016/0331600 A1 | 11/2016 | Polidori |
| 2018/0070041 A1 | 3/2018 | Hirota |
| 2018/0168877 A1 | 6/2018 | Schneider |
| 2018/0168878 A1 | 6/2018 | Schneider |
| 2018/0168879 A1 | 6/2018 | Schneider |
| 2018/0168880 A1 | 6/2018 | Schneider |
| 2018/0169964 A1 | 6/2018 | Schneider |
| 2018/0170026 A1 | 6/2018 | Schneider |
| 2018/0170027 A1 | 6/2018 | Schneider |
| 2018/0228656 A1 | 8/2018 | Schneider |
| 2018/0228666 A1 | 8/2018 | Trinkaus |
| 2018/0228668 A1 | 8/2018 | Schneider |
| 2021/0016518 A1 | 1/2021 | Schneider |
| 2023/0310228 A1* | 10/2023 | Minami ............ A61F 13/51104 604/358 |

OTHER PUBLICATIONS

Extended European Search Report and Search Opinion; Application No. 20180572.8; dated Dec. 1, 2020, 5 pages.

* cited by examiner

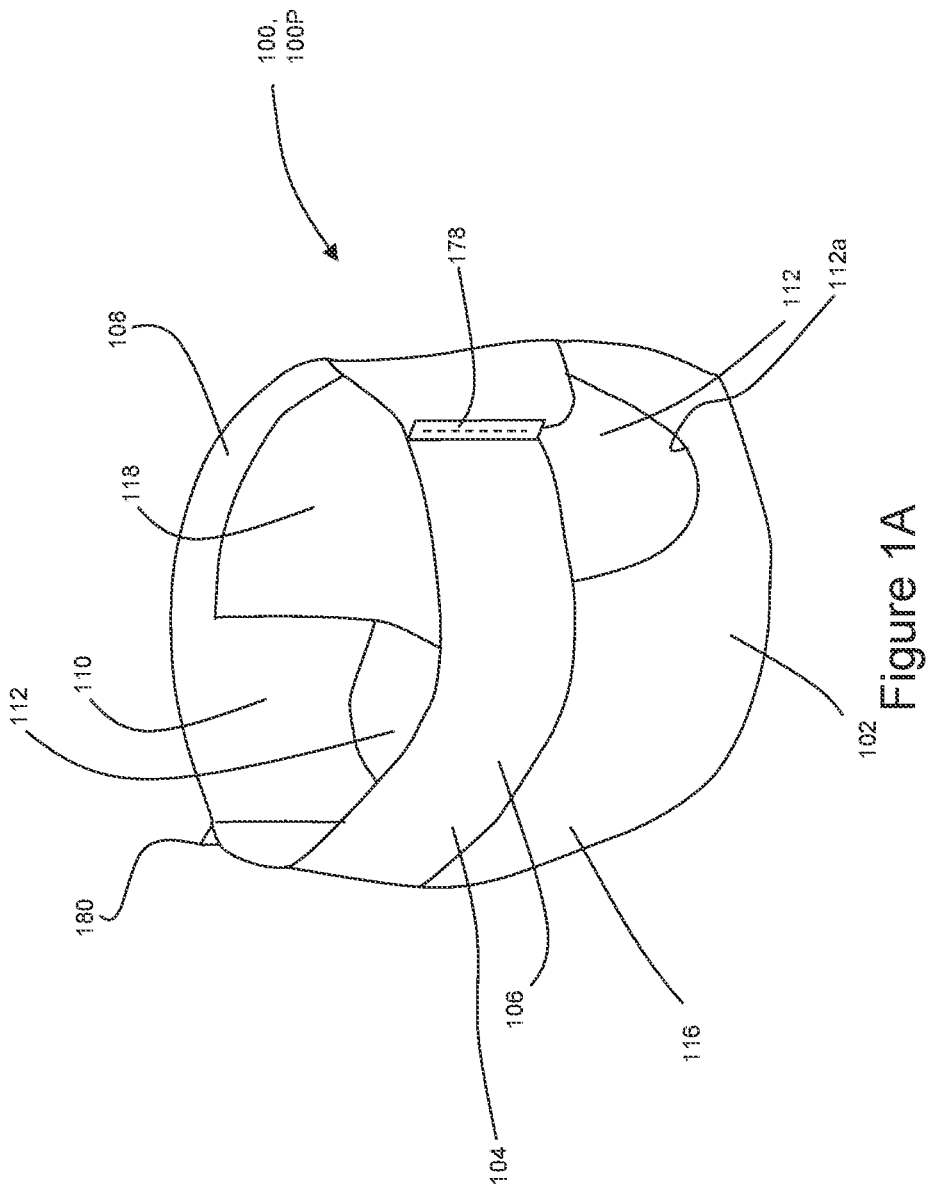

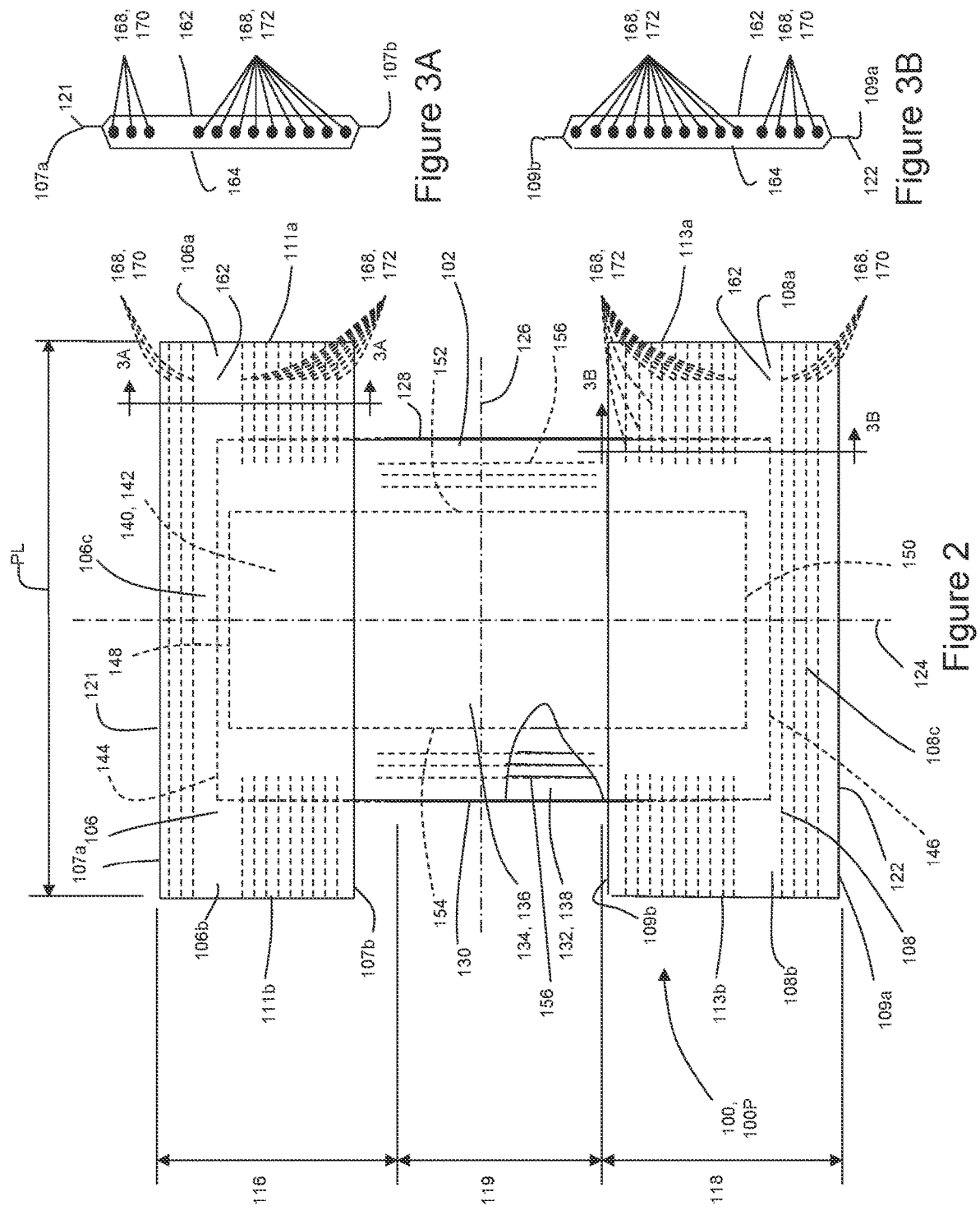

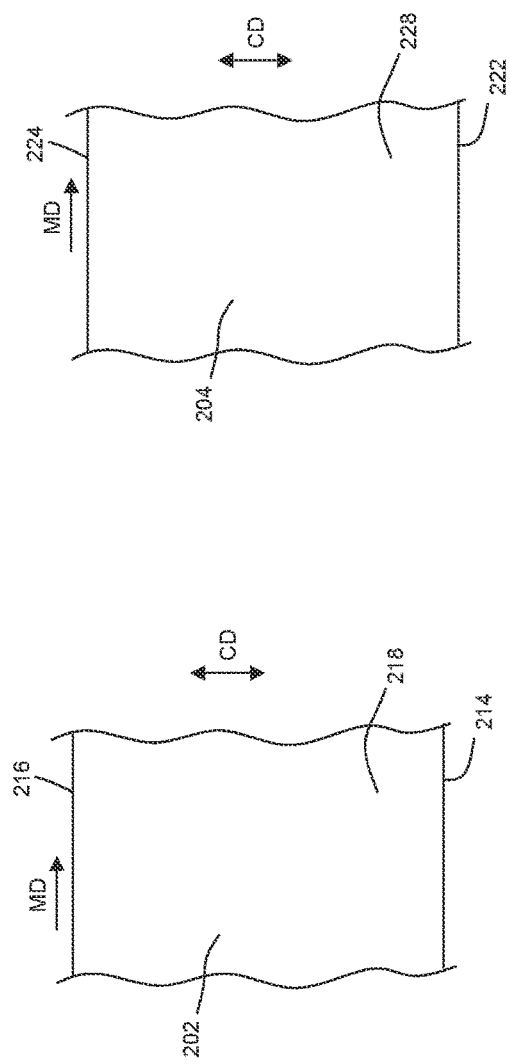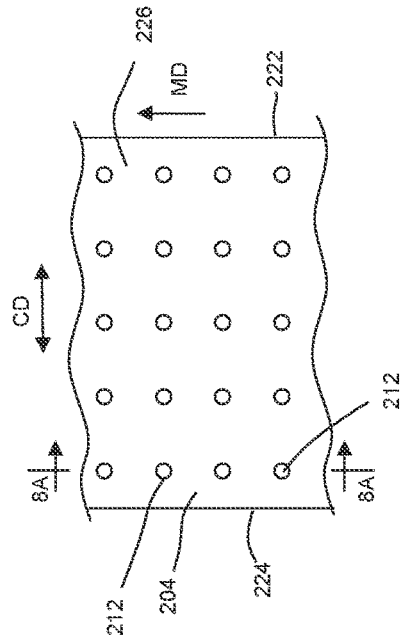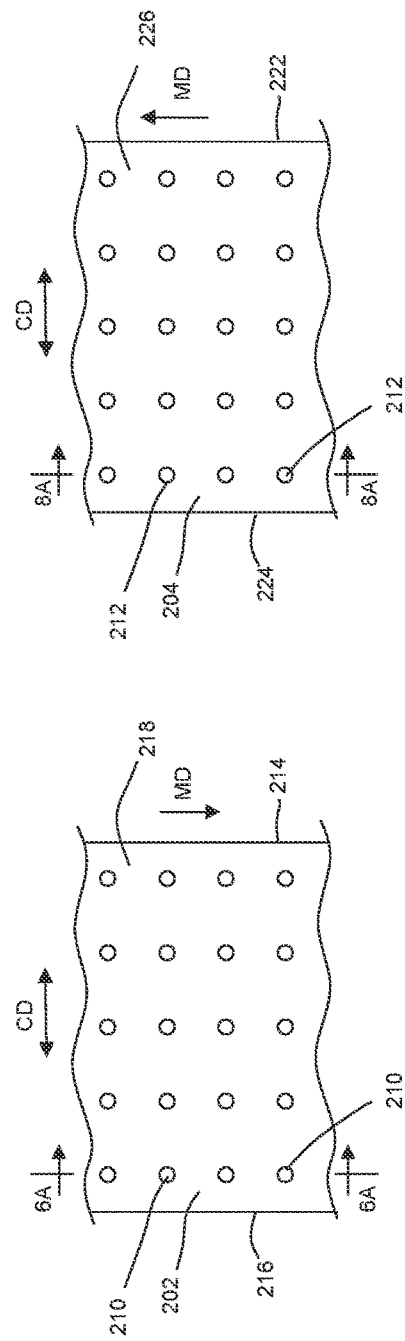

METHOD AND APPARATUS FOR ASSEMBLING APERTURED ELASTIC LAMINATES

CROSS REFERENCE TO RELATED APPLICATIONS

This application is a divisional of U.S. patent application Ser. No. 16/903,501, filed on Jun. 17, 2020, which claims the benefit of U.S. Provisional Patent Application Ser. No. 62/874,600, filed on Jul. 16, 2019, both of which are hereby incorporated by reference herein.

FIELD OF THE INVENTION

The present disclosure relates to methods for manufacturing absorbent articles, and more particularly, to apparatuses and methods for making apertured elastic laminates that may be used as components of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some absorbent articles have components that include elastic laminates. Such elastic laminates may include an elastic material bonded between two substrates. The elastic material may include an elastic film and/or elastic strands. In some laminates, elastic strands are joined between two nonwovens while the elastic strands are in a stretched condition so that when the elastic strands relax, the nonwovens gather between the locations where the nonwovens are bonded to each other, and in turn, forms corrugations. The resulting elastic laminate is stretchable to the extent that the corrugations allow the elastic strands to elongate.

In some assembly processes, stretched elastic strands may be advanced in a machine direction and bonded between two advancing nonwovens to create an elastic laminate, wherein the stretched elastic strands are spaced apart from each other in a cross direction. Depending on where or how an elastic laminate may be used in an assembled product, it may be desirable to enhance certain features of the elastic laminate. For example, if the elastic laminate is assembled for the purpose of being converted into an elastic belt on a diaper pant, it may be desirable to increase the breathability of the elastic laminate to help enhance a wearer's comfort during use of the diaper pant.

As such, the nonwovens may be subjected to a perforating or aperturing process during assembly to form apertures in the nonwovens. In turn, the apertures may help increase the breathability of the elastic laminate. However, advancement of the nonwovens between separate assembly operations and the stretchability of the nonwovens can increase the difficulty in aligning the apertures in the individual nonwovens with respect to each other and/or the bonding processes during laminate assembly. In turn, misalignment or misplacement of the apertures in the nonwovens may result in apertures being blocked or covered by the opposing nonwovens and/or by the bonds between the two substrates. Unintentional blocking of such apertures, may in turn, detract from the breathability of the assembled laminate.

In an attempt to overcome the aforementioned problems associated with aperturing the individual nonwovens, some assembly processes may be configured to aperture the assembled laminate after assembly. However, subjecting an assembled elastic laminate to aperturing processes can detract from other desirable features of the elastic laminate, such as softness. For example, in some aperturing processes, apertures are created in the elastic laminate by inserting pins or needles through the laminate. When inserting pins through the laminate, the nonwovens may be deformed and protrusions may be created where the apertures are formed. Such protrusions may extend outward from one surface of the laminate. As such, the surface of the resulting laminate that includes the protrusions protruding therefrom may feel relatively rough.

Consequently, it would be beneficial to provide elastic laminates and methods and apparatuses for producing such elastic laminates wherein apertures are positioned in desired locations with respect to each other and/or with respect to bond regions while not detracting from the softness of the assembled laminate.

SUMMARY OF THE INVENTION

In one form, a method for making absorbent articles comprises steps of: forming first apertures in a first substrate, the first substrate comprising a first surface and an opposing second surface; advancing elastic material onto the second surface of the first substrate; forming second apertures in a second substrate, the second substrate comprising a first surface and an opposing second surface; advancing the second substrate onto the first substrate and elastic material to form a laminate, wherein the first surface of the second substrate is in a facing relationship with the second surface of the first substrate; and bonding the first substrate with the second substrate in bond regions, wherein the bond regions are separated from each other along the machine direction to define unbonded regions, wherein the first apertures and the second apertures are positioned in the unbonded regions.

In another form, a method for making absorbent articles comprises steps of: providing a combining roll comprising an outer circumferential surface; providing a first aperturing device comprising a first roll and first pin members, the first roll adjacent the combining roll to define a first nip therebetween; providing a second aperturing device comprising a second roll and second pin members, the second roll adjacent the combining roll to define a second nip therebetween; advancing a first substrate to the first aperturing device, the first substrate comprising a first surface and an opposing second surface; forming first apertures in the first substrate by penetrating the first substrate with the first pin members; advancing first substrate through the first nip from the first roll of the first aperturing device onto the combining roll with the first surface in a facing relationship with the outer circumferential surface; stretching elastic strands in a machine direction; advancing the stretched elastic strands onto the second surface of the first substrate on the combining roll; advancing a second substrate to the second aperturing device, the second substrate comprising a first surface and an opposing second surface; forming second apertures in the second substrate by penetrating the second substrate with the second pin members; advancing the second substrate through the second nip from the second roll onto the first substrate and the stretched elastic strands on the combining roll to form a laminate, wherein the first surface of the second substrate is in a facing relationship with the second surface of the first substrate; advancing the laminate on the combining roll in the machine direction; and bonding the first substrate with the second substrate of the laminate in bond regions, wherein the bond regions are separated from each other along the machine direction by unbonded regions, wherein the first apertures and the second apertures are positioned in the unbonded regions.

In yet another form, an absorbent article comprises: an elastic laminate comprising: a first substrate comprising a first surface and an opposing second surface, and first apertures surrounded by first protuberances extending outward from second surface; a second substrate comprising a first surface and an opposing second surface, and second apertures surrounded by second protuberances extending outward from the first surface; elastic strands positioned between the first and second substrates; the first substrate bonded with the second substrate in bond regions, wherein the second surface of the first substrate is in a facing relationship with the first surface of the second substrate, and wherein the bond regions are separated from each other by unbonded regions, and wherein the first apertures and the second apertures are positioned in the unbonded regions; and an absorbent chassis connected with the elastic laminate.

In still another form, a method for making absorbent articles comprises steps of: forming first apertures in a first substrate, the first substrate comprising a first surface and an opposing second surface; advancing elastic material onto the second surface of the first substrate; providing a second substrate, the second substrate comprising a first surface and an opposing second surface; advancing the second substrate onto the first substrate and elastic material to form a laminate, wherein the first surface of the second substrate is in a facing relationship with the second surface of the first substrate; bonding the first substrate with the second substrate in bond regions, wherein the bond regions are separated from each other along the machine direction to define unbonded regions; and removing tension from the laminate to form first corrugations in the first substrate and to form second corrugations in the second substrate, the first and second corrugations positioned between the bond regions, and wherein the first apertures are positioned in the first corrugations.

BRIEF DESCRIPTION OF THE DRAWINGS

FIG. 1A is a front perspective view of a diaper pant.
FIG. 2 is a partially cut away plan view of the diaper pant shown in FIGS. 1A and 1B in a flat, uncontracted state.
FIG. 3A is a cross-sectional view of the diaper pant of FIG. 2 taken along line 3A-3A.
FIG. 3B is a cross-sectional view of the diaper pant of FIG. 2 taken along line 3B-3B.

FIG. 5 is a view of a first substrate taken along section 5-5 in FIGS. 4A, 4B, and 4C.
FIG. 6 is a view of the first substrate with first apertures taken along section 6-6 in FIGS. 4A, 4B, and 4C.
FIG. 7 is a view of a second substrate taken along section 7-7 in FIGS. 4A, 4B, and 4C.
FIG. 8 is a view of the second substrate with second apertures taken along section 8-8 in FIGS. 4A, 4B, and 4C.

DETAILED DESCRIPTION OF THE INVENTION

Figure 1B:
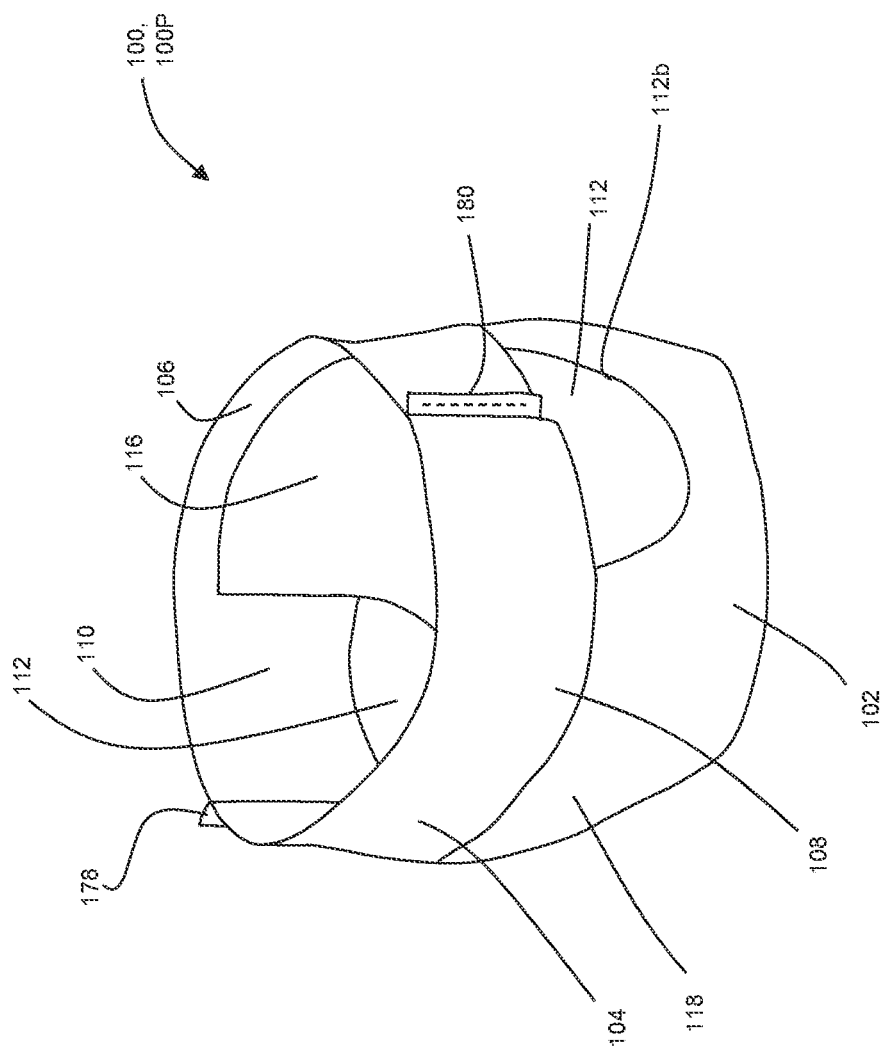
FIG. 1B is a rear perspective view of a diaper pant.

The following term explanations may be useful in understanding the present disclosure:

"Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The terms "registration process," "registration system," "registration," "register," "registered," or "registering" as used herein refer to a machine control process or system for controlling a substrate or laminate, (which can have multiplicity of pre-produced objects, such as apertures, bonds, graphics, patterns, design elements, and/or insignia spaced on the substrate or laminate at a pitch interval that may vary in the machine direction) through a converting line producing articles, by providing a positional adjustment of the pre-produced objects on the substrate or laminate to a target position constant associated with a pitched unit operation of the converting line.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897,545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

The present disclosure relates to methods for manufacturing absorbent articles, and in particular, to methods for making apertured elastic laminates that may be used as components of absorbent articles. With regard to the assembly processes described herein, first apertures are formed in a first substrate. Elastic material, such as elastic strands, is stretched in a machine direction and is advanced onto the first substrate. Second apertures are formed in a second substrate, and the second substrate is advanced onto the first substrate and elastic material to form a laminate. The first substrate is bonded with the second substrate in bond regions, wherein the bond regions are separated from each other along the machine direction to define unbonded regions, wherein the first apertures and the second apertures are positioned in the unbonded regions. Tension may be removed from the laminate to allow the elastic material to contract and to form first corrugations in the first substrate and form second corrugations in the second substrate, wherein the first and second corrugations are positioned between the bond regions.

As discussed below, the methods and apparatuses may be close coupled such that materials may advance directly between aperturing and bonding operations. Such close coupling of devices may help to more precisely control the positions of the apertures in substrates relative to positions of apertures opposing substrates and/or bonds in the assembled laminate. Enhanced control of the positions of the apertures may help reduce and/or eliminate situations wherein apertures are unintentionally covered or blocked by another substrate and/or by bonds between the substrates. In some configurations, first apertures in the first substrate may be aligned with second apertures in the second substrate to define apertures that extend through the laminate. In some configurations, apertures may be positioned on peaks of the corrugations in either or both the substrates of the laminate in a relaxed condition. In yet other configurations, one or more apertures may be positioned on walls of the corrugations in either or both the substrates of the laminate in a relaxed condition. As discussed in more detail below, one or both the substrates may be apertured prior to laminate assembly, and the aperturing process may also deform a substrate and create protrusions or protuberances extending from one surface of the substrate. In turn, the methods and apparatuses herein provide the ability to orient protrusions or protuberances in the substrates created by the aperturing process so as to extend inward and away from both outer surfaces of the assembled laminate. As such, the assembly process may be conducted so as to mitigate reductions in softness that might otherwise result from the aperturing process in the assembled laminate.

FIGS. 1A, 1B, and 2 show an example of an absorbent article 100 in the form of a diaper pant 100P that may include components constructed from elastic laminates assembled in accordance with the apparatuses and methods disclosed herein. In particular, FIGS. 1A and 1B show perspective views of a diaper pant 100P in a pre-fastened configuration, and FIG. 2 shows a plan view of the diaper pant 100P with the portion of the diaper that faces away from a wearer oriented toward the viewer. The diaper pant 100P includes a chassis 102 and a ring-like elastic belt 104. As discussed below in more detail, a first elastic belt 106 and a second elastic belt 108 are bonded together to form the ring-like elastic belt 104.

With continued reference to FIG. 2, the diaper pant 100P and the chassis 102 each include a first waist region 116, a second waist region 118, and a crotch region 119 disposed intermediate the first and second waist regions. The first waist region 116 may be configured as a front waist region, and the second waist region 118 may be configured as back waist region. The diaper 100P may also include a laterally extending front waist edge 121 in the front waist region 116 and a longitudinally opposing and laterally extending back waist edge 122 in the back waist region 118. To provide a frame of reference for the present discussion, the diaper 100P and chassis 102 of FIG. 2 are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1A, 1B, and 2, the diaper pant 100P may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100P may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100P is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

As previously mentioned, the diaper pant 100P may include a backsheet 136. The backsheet 136 may also define the outer surface 134 of the chassis 102. The backsheet 136 may also comprise a woven or nonwoven material, polymeric films such as thermoplastic films of polyethylene or polypropylene, and/or a multi-layer or composite materials comprising a film and a nonwoven material. The backsheet may also comprise an elastomeric film. An example backsheet 136 may be a polyethylene film having a thickness of from about 0.012 mm (0.5 mils) to about 0.051 mm (2.0 mils). Further, the backsheet 136 may permit vapors to escape from the absorbent core (i.e., the backsheet is breathable) while still preventing exudates from passing through the backsheet 136.

Also described above, the diaper pant 100P may include a topsheet 138. The topsheet 138 may also define all or part of the inner surface 132 of the chassis 102. The topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art. Topsheets 138 may be selected from high loft nonwoven topsheets, apertured film topsheets and apertured nonwoven topsheets. Exemplary apertured films may include those described in U.S. Pat. Nos. 5,628,097; 5,916,661; 6,545,197; and 6,107,539, all of which are incorporated by reference herein.

As mentioned above, the diaper pant 100P may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735, all of which are incorporated by reference herein.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1, all of which are incorporated by reference herein.

As previously mentioned, the diaper 100P may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730 A1, all of which are incorporated by reference herein.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIGS. 1A and 1B. The ring-like elastic belt may be formed by joining a first elastic belt to a second elastic belt with a permanent side seam or with an openable and reclosable fastening system disposed at or adjacent the laterally opposing sides of the belts.

As previously mentioned, the ring-like elastic belt 104 may be defined by a first elastic belt 106 connected with a second elastic belt 108. As shown in FIG. 2, the first elastic belt 106 extends between a first longitudinal side edge 111a and a second longitudinal side edge 111b and defines first and second opposing end regions 106a, 106b and a central region 106c. And the second elastic 108 belt extends between a first longitudinal side edge 113a and a second longitudinal side edge 113b and defines first and second opposing end regions 108a, 108b and a central region 108c. The distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108. The central region 106c of the first elastic belt is connected with the first waist region 116 of the chassis 102, and the central region 108c of the second elastic belt 108 is connected with the second waist region 118 of the chassis 102. As shown in FIGS. 1A and 1B, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer laterally extending edge 107a and an inner laterally extending edge 107b, and the second elastic belt 108 defines an outer laterally extending edge 109a and an inner laterally extending edge 109b. As such, a perimeter edge 112a of one leg opening may be defined by portions of the inner laterally extending edge 107b of the first elastic belt 106, the inner laterally extending edge 109b of the second elastic belt 108, and the first longitudinal or right side edge 128 of the chassis 102. And a perimeter edge 112b of the other leg opening may be defined by portions of the inner laterally extending edge 107b, the inner laterally extending edge 109b, and the second longitudinal or left side edge 130 of the chassis 102. The outer laterally extending edges 107a, 109a may also define the front waist edge 121 and the laterally extending back waist edge 122 of the diaper pant 100P. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer substrate layer 162 and the inner substrate layer 164. The belt elastic material may include one or more elastic elements such as strands, ribbons, films, or panels extending along the lengths of the elastic belts. As shown in FIGS. 2, 3A, and 3B, the belt elastic material may include a plurality of elastic strands 168 which may be referred to herein as outer, waist elastics 170 and inner, waist elastics 172. Elastic strands 168, such as the outer waist elastics 170, may continuously extend laterally between the first and second opposing end regions 106a, 106b of the first elastic belt 106 and between the first and second opposing end regions 108a, 108b of the second elastic belt 108. In some embodiments, some elastic strands 168, such as the inner waist elastics 172, may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2. The belt elastic material may be joined to the outer and/or inner layers continuously or intermittently along the interface between the belt elastic material and the inner and/or outer belt layers.

In some configurations, the first elastic belt 106 and/or second elastic belt 108 may define curved contours. For example, the inner lateral edges 107b, 109b of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168, 172 that extend along non-linear or curved paths that may correspond with the curved contours of the inner lateral edges 107*b*, 109*b*.

It is to be appreciated that the apparatuses and methods of assembly of elastic laminates and absorbent articles described herein and illustrated in the accompanying drawings are non-limiting example configurations. The features illustrated or described in connection with one non-limiting configuration may be combined with the features of other non-limiting configurations. Such modifications and variations are intended to be included within the scope of the present disclosure.

Figure 4A:
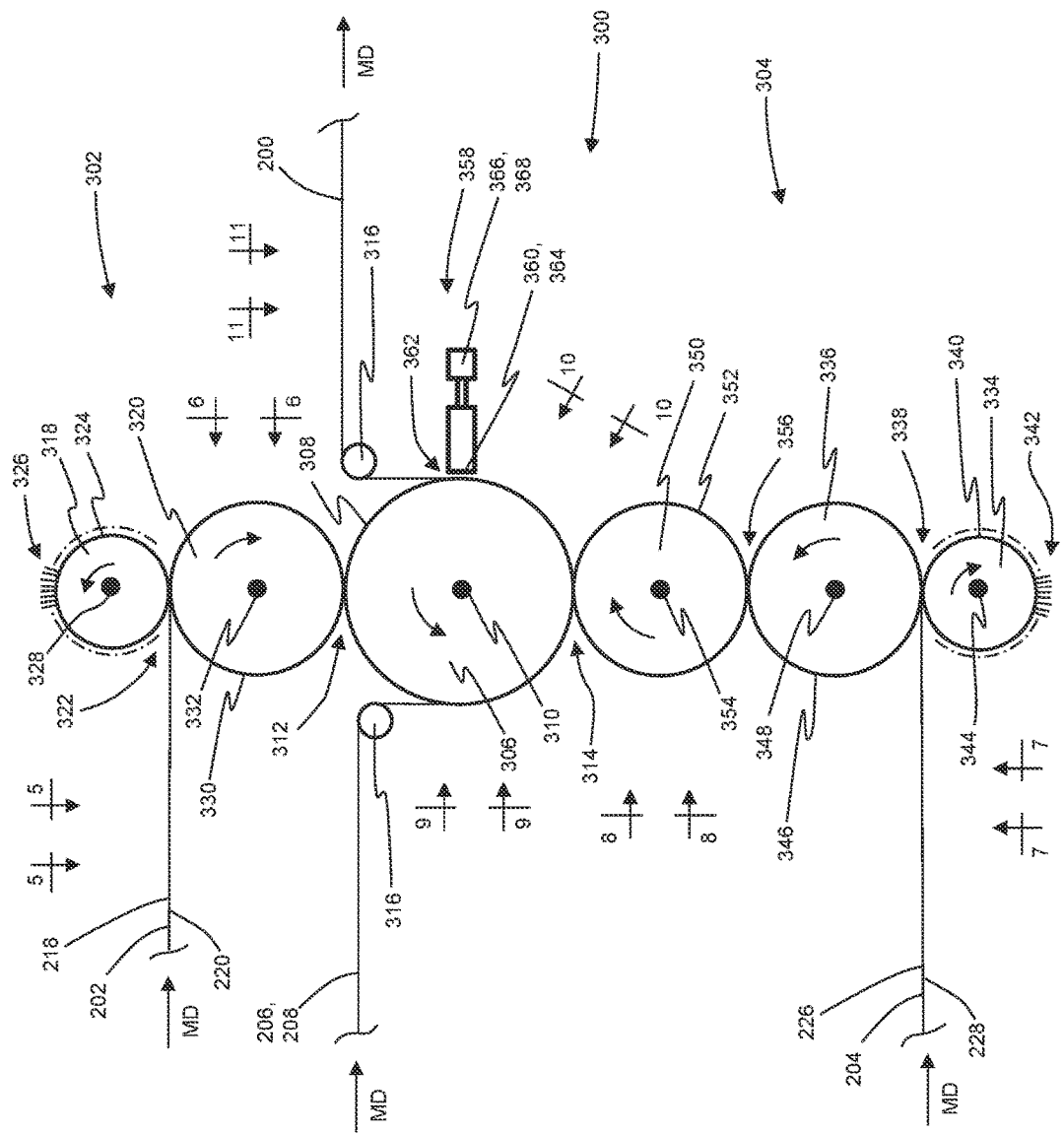
FIG. 4A is a schematic side view of a converting apparatus adapted to assemble an apertured elastic laminate.
Figure 4B:
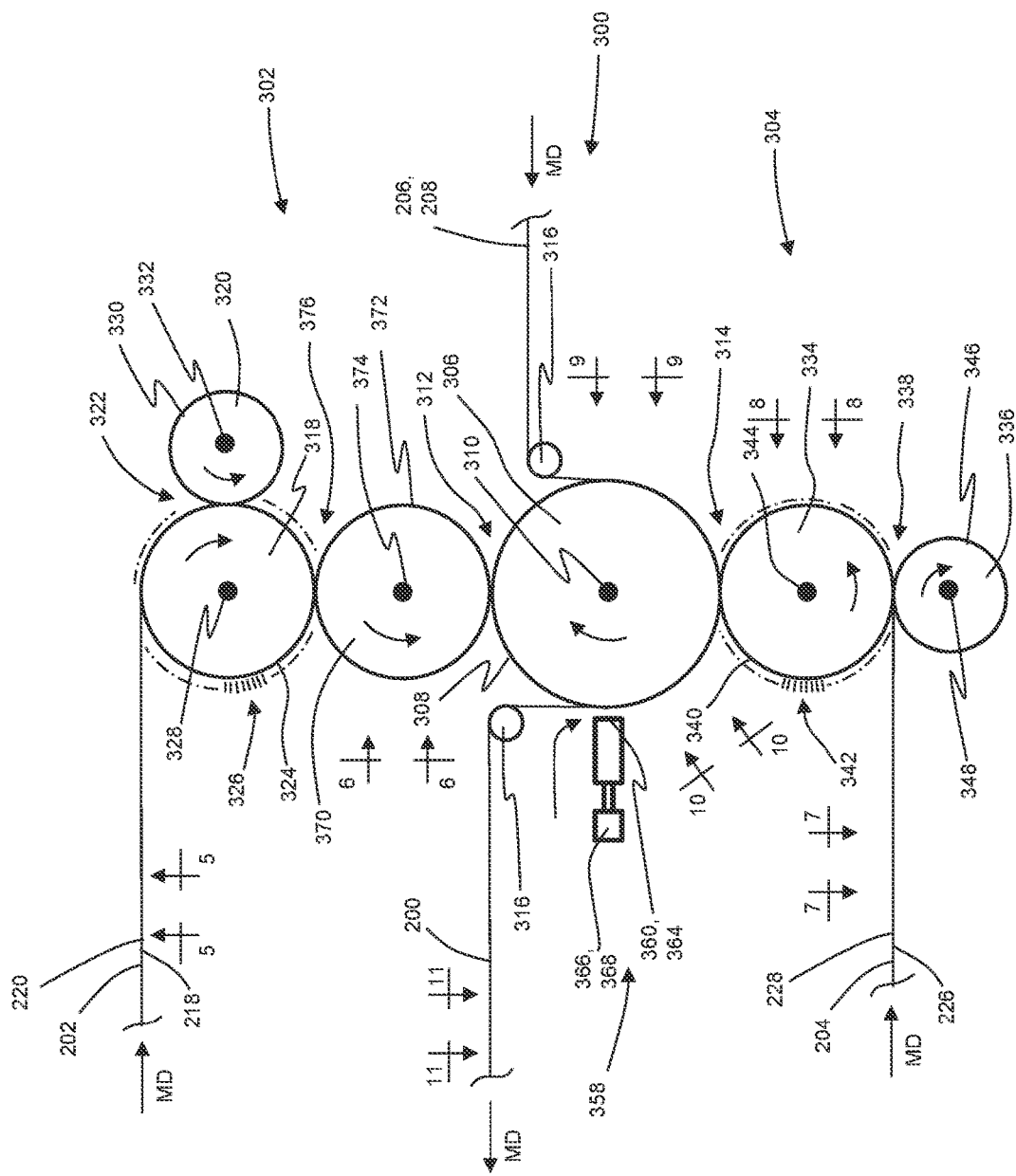
FIG. 4B is a schematic side view of another configuration of a converting apparatus adapted to manufacture an apertured elastic laminate.
Figure 4C:
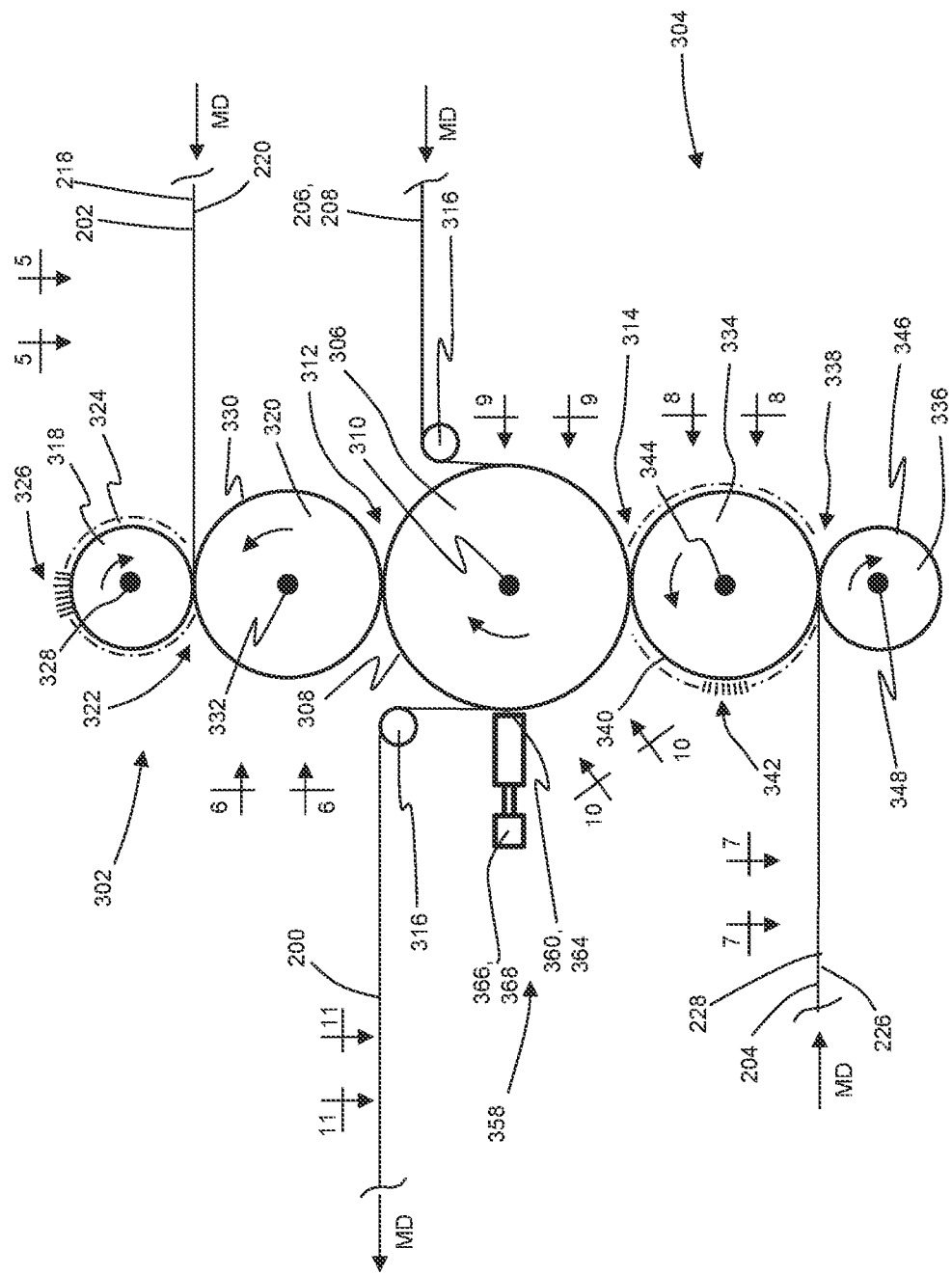
FIG. 4C is a schematic side view of another configuration of a converting apparatus adapted to manufacture an apertured elastic laminate.

As previously mentioned, apparatuses and methods according to the present disclosure may be utilized to produce elastic laminates that may be used to construct various components of absorbent articles, such as elastic belts, leg cuffs, and the like. For example, FIGS. 4A-4C show schematic views of converting apparatuses 300 adapted to manufacture elastic laminates 200. As described in more detail below, the converting apparatuses 300 operate to advance a continuous length of a first substrate 202, a continuous length of a second substrate 204, and a continuous length of elastic material 206 along a machine direction MD. It is also to be appreciated that in some configurations, the first substrate 202 and second substrate 204 herein may be defined by two discrete single layer substrates or may be defined by multi-layered laminates. And in some configurations, the first substrate 202 and/or the second substrate 204 may comprise nonwovens. The apparatus 300 forms apertures in either or both the first substrate 202 and the second substrate 204. The apparatus may also stretch the elastic material 206 and join the stretched elastic material 206 with the first and second substrates 202, 204 to produce an elastomeric laminate 200. Although the elastic material 206 is illustrated and referred to herein as elastic strands 208, it is to be appreciated that elastic material 206 may include one or more continuous lengths of elastic strands, ribbons, and/or films.

As shown in FIG. 4A a converting apparatus 300 for producing an elastic laminate 200 may include a first aperturing device 302 and a second aperturing device 304 positioned adjacent a combining roll 306. The combining roll 306 may include an outer circumferential surface 308 adapted to rotate about an axis 310. The first aperturing device 302 may be positioned adjacent the combining roll 306 to define a first combining nip 312 therebetween, and the second aperturing device 304 may be positioned adjacent the combining roll 306 to define a second combining nip 314 therebetween. In some configurations, a component, such as a roll discussed below, of the first aperturing device 302 may be in direct contact with the combining roll 306 or may be separated from the combining roll 306 such that a relatively short span of the first substrate 202 advances through the first combining nip 312 during operation. In some configurations, a component, such as a roll discussed below, of the second aperturing device 304 may be in direct contact with the combining roll 306 or may be separated from the combining roll 306 such that a relatively short span of the second substrate 204 advances through the second combining nip 314 during operation. As shown in FIGS. 4A and 5-8, the first aperturing device 302 is configured to form first apertures 210 in the first substrate 202, and the second aperturing device 304 is configured to form second apertures 212 in the second substrate 204. As shown in FIGS. 4A, 5, and 6, the first substrate 202 comprises a first longitudinal edge 214 and a second longitudinal edge 216 separated from the first longitudinal edge 214 in the cross direction CD to define a width. The first substrate 202 also includes a first surface 218 and an opposing second surface 220. Similarly, as shown in FIGS. 4A, 7, and 8, the second substrate 204 comprises a first longitudinal edge 222 and a second longitudinal edge 224 separated from the first longitudinal edge 222 in the cross direction CD to define a width. The second substrate 204 also includes a first surface 226 and an opposing second surface 228.

With reference to FIGS. 4A and 5-11, during operation, the first substrate 202 advances from the first aperturing device 302 through the first combining nip 312 and onto the combining roll 306. Elastic strands 208 that are stretched in the machine direction MD may also advance in the machine direction MD onto the first substrate 202 on the combining roll 306. The second substrate 204 may advance from the second aperturing device 304 through the second combining nip 314 and onto the first substrate 202 and stretched elastic strands 208 on the combining roll 306 to form the laminate 200. In turn, the first substrate 202 and the second substrate 204 are bonded together in bond regions 230, wherein the bond regions 230 are separated from each other along the machine direction MD to define unbonded regions 232. The first apertures 210 and the second apertures 212 may be positioned in the unbonded regions 232. It is to be appreciated that the first substrate 202 and the second substrate 204 may be bonded together in various ways, such as by heat, pressure, ultrasonic energy, and/or adhesive applied to at least one of the first substrate 202 and the second substrate 204. In addition, the first substrate 202 and the second substrate 204 may be bonded together while positioned on the combining roll 306 or downstream of the combining roll 306. As shown in FIG. 4A, the apparatuses 300 herein may also include one or more guide rolls 316 that may be arranged to guide the first substrate 202, the second substrate 204, and/or elastic material 206 to and/or from the aperturing devices 302, 304 and/or the combining roll 306.

As shown in FIG. 4A, the first aperturing device 302 may include a first perforator roll 318 adjacent a first anvil roll 320 to define a first aperturing nip 322 therebetween. The first perforator 318 roll may include an outer circumferential surface 324 and first pin members 326 or needles protruding radially outward and adapted to rotate about an axis 328. The first anvil roll 320 may include an outer circumferential surface 330 adapted to rotate about an axis 332 in a direction opposite the first perforator roll 318. The first anvil roll 320 may be arranged such that the first combining nip 312 is defined between the first anvil roll 320 and the combining roll 306, and wherein the first anvil roll 320 and the combining roll 306 rotate in opposite directions. The first substrate 202 may advance in the machine direction MD to the first aperturing device 302 with the second surface 220 of the first substrate 202 in a facing relationship with the outer circumferential surface 330 of the first anvil roll 320. The first substrate 202 advances through the first aperturing nip 322 where the first pin members 326 penetrate the first substrate 202 and form first apertures 210 in the first substrate 202.

Figure 6A:
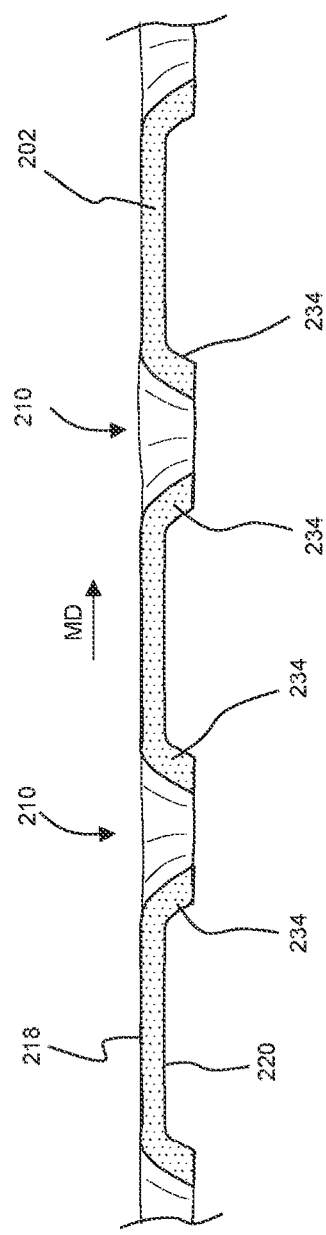
FIG. 6A is a view of the first substrate with first apertures taken along section 6A-6A in FIG. 6.
Figure 6B:
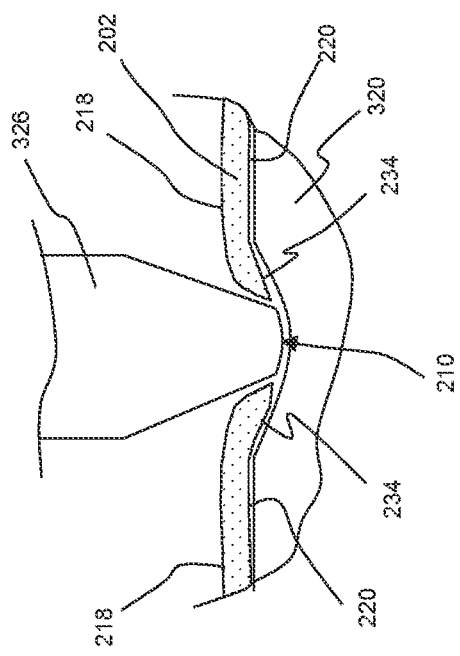
FIG. 6B is a detailed view of a pin member penetrating the first substrate.

As shown in FIGS. 4A, 6A, and 6B, the first pin members 326 may be directed from the first surface 218 toward the second surface 220 of the first substrate 202. As the first pin members 326 penetrate the first substrate 202, the first pin members 326 may deform the first substrate 202 to define first protuberances 234 extending outward from second surface 220. In some configurations, the first protuberances 234 may comprise substantially frustoconical shaped sides. With continued reference to FIG. 4A, the first substrate 202 may advance on the outer circumferential surface 330 of the first anvil roll 320 from the first aperturing nip 322 and through the first combining nip 312. As such, the first substrate 202 is transferred onto the combining roll 306 with the first surface 218 of the first substrate 202 in a facing relationship with the outer circumferential surface 308 of the combining roll 306. As such, the first protuberances 234 extend radially outward from the combining roll 306.

Figure 9:
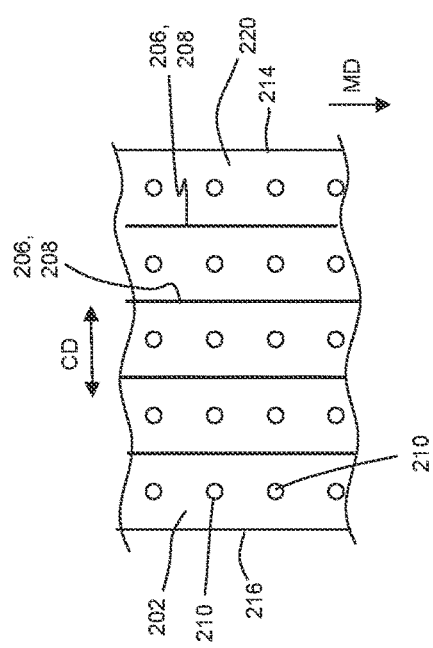
FIG. 9 is a view of elastics strands and the first substrate taken along section 9-9 in FIGS. 4A, 4B, and 4C.

With reference to FIGS. 4A and 9, elastic strands 208 are advanced in the machine direction MD to the combining roll 306 and onto the second surface 220 of the first substrate 202. The elastic strands 208 are separated from each other in the cross direction CD and are stretched in the machine direction MD. In some configurations, the elastic strands 208 may be advanced to the combining roll 306 in a stretched state. In some configurations, the combining roll 306 may rotate such that the outer circumferential surface 308 advances at a higher speed than a speed at which the elastic stands 208 are advanced to the combining roll 306, which in turn, stretches the elastic strands 208 while advancing onto the combining roll 306. It is also to be appreciated that the elastic strands 208 may be supplied to the combining roll 306 in various ways and/or with various types of elastic unwinder configurations, such as beams, overend unwinder or surface driven unwinder and unwinders, such as disclosed for example in U.S. Pat. Nos. 6,676,054; 7,878,447; 7,905,446; and 9,156,648 and U.S. Patent Publication Nos. 2018/0168878 A1; 2018/0168877 A1; 2018/0168880 A1; 2018/0170027 A1; 2018/0169964 A1; 2018/0168879 A1; 2018/0170026 A1; and 2018/0070041 A1, which are all incorporated by reference herein.

Referring now to FIG. 4A, the second aperturing device 304 may include a second perforator roll 334 adjacent a second anvil roll 336 to define a second aperturing nip 338 therebetween. The second perforator roll 334 may include an outer circumferential surface 340 and second pin members 342 or needles protruding radially outward and adapted to rotate about an axis 344. The second anvil roll 336 may include an outer circumferential surface 346 adapted to rotate about an axis 348 in a direction opposite the second perforator roll 334. The second aperturing device 304 may also include a transfer roll 350 that may include an outer circumferential surface 352 adapted to rotate about an axis 354 in a direction opposite the second anvil roll 336. The transfer roll 350 may be arranged such that a transfer nip 356 is defined between the transfer roll 350 and the second anvil roll 336. The transfer roll 350 may also be arranged such that the second combining nip 314 is defined between the transfer roll 350 and the combining roll 306, and wherein the transfer roll 350 and the combining roll 306 rotate in opposite directions. The second substrate 204 may advance in the machine direction MD to the second aperturing device 304 with the first surface 226 of the second substrate 204 in a facing relationship with the outer circumferential surface 346 of the second anvil roll 336. The second substrate 204 advances through the second aperturing nip 338 where the second pin members 342 penetrate the second substrate 204 and form second apertures 212 in the second substrate 204.

Figure 8A:
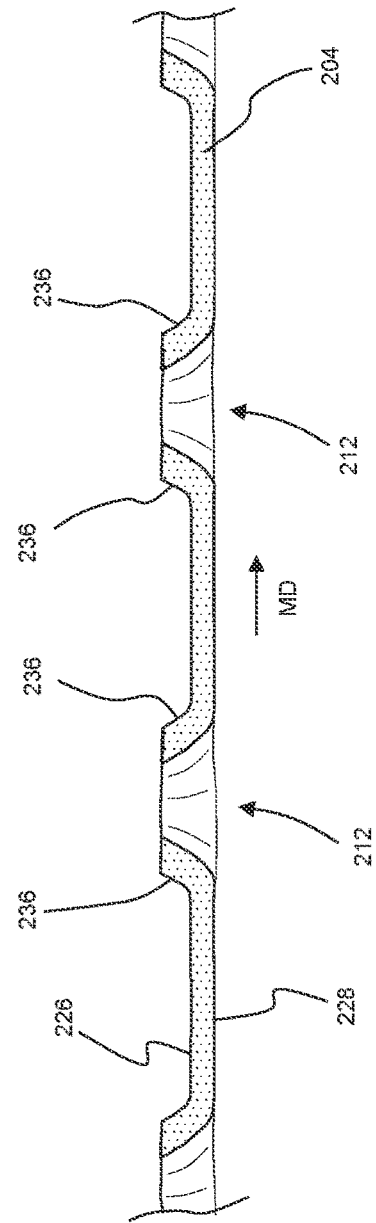
FIG. 8A is a view of the second substrate with second apertures taken along section 8A-8A in FIG. 8.
Figure 8B:
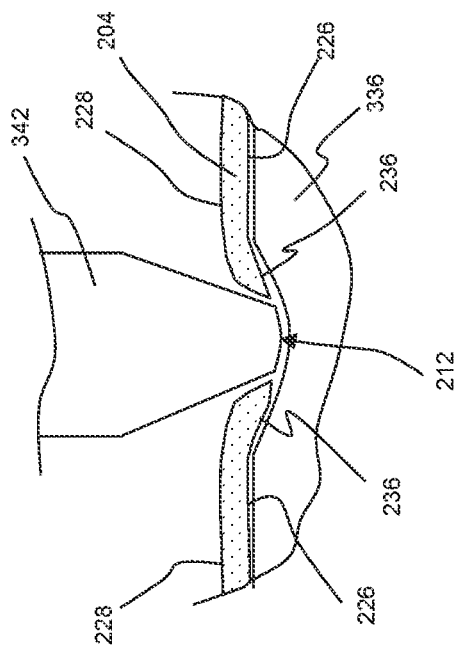
FIG. 8B is a detailed view of a pin member penetrating the second substrate.

As shown in FIGS. 4A, 8A, and 8B, the second pin members 342 may be directed from the second surface 228 toward the first surface 226 of the second substrate 204. As the second pin members 342 penetrate the second substrate 204, the second pin members 342 may deform the second substrate 204 to define second protuberances 236 extending outward from the first surface 226. In some configurations, the second protuberances 236 may comprise substantially frustoconical shaped sides. With reference to FIG. 4A, the second substrate may advance on the outer circumferential surface 346 of the second anvil roll 336 from the second aperturing nip 338 and through the transfer nip 356. As such, the second substrate 204 is transferred onto the transfer roll 350 with the second surface 228 of the second substrate 204 in a facing relationship with the outer circumferential surface 352 of the transfer roll 350. As such, the second protuberances 236 extend radially outward from the transfer roll 350. In turn, the second substrate 204 may advance on the outer circumferential surface 352 of the transfer roll 350 from the transfer nip 356 and through the second combining nip 314. As such, the second substrate 204 is transferred onto the combining roll 306 with the first surface 226 of the second substrate 204 in a facing relationship with second surface 220 of the first substrate 202 and stretched elastic strands 208 on the combining roll 306 to form the elastic laminate 200. As such, the second protuberances 236 extend radially inward toward the outer circumferential surface 308 of the combining roll 306.

As shown in FIGS. 4A, 10, 10A, 11, and 11A, the elastic laminate 200 may advance on the outer circumferential surface 308 of the combining roll 306 to a bonding device 358 that bonds the first substrate 202 and the second substrate 204 together in bond regions 230. It is to be appreciated that the bonding device 358 may be configured in various ways. For example, as shown in FIG. 4A, the bonding device 358 may be configured to include the combining roll 306 and a pressing surface 360 adjacent the combining roll 306 to define a nip 362 therebetween. During operation, combining roll 306 rotates to advance the elastic laminate 200 through the nip 362 between the combining roll 306 and the pressing surface 360 to mechanically bond the first substrate 202 and the second substrate 204 together. The combining roll 306 may also be configured to apply vacuum pressure to the elastic laminate 200 to help hold the first and second substrates 202, 204 on the outer circumferential surface 308 as the combining roll 306 rotates.

With continued reference to FIG. 4A, the bonding device 358 may be configured as a mechanical bonding device, wherein the combining roll 306 may be configured as a pattern roll. As such, the outer circumferential surface 308 of the combining roll 306 may also comprise one or more bonding surfaces defined by bonding elements extending radially outward. As the combining roll 306 rotates, the elastic laminate 200 is advanced between the bonding surfaces and the pressing surface 360 to mechanically bond or weld the first substrate 202 and the second substrate 204 together to create bond regions 230 between the between the first substrate 202 and the second substrate 204. Heat and/or pressure between the pressing surface 360 and the combining roll 306 may melt and bond the first and second substrates 202, 204 together in areas supported by the bonding surfaces on the combining roll 306. As such, the mechanical bonds and/or bond regions 230 may have shapes that correspond with and may mirror shapes of the bonding surfaces.

It is to be appreciated that the pressing surface 360 may be configured in various ways. For example, as shown in FIG. 4A, the pressing surface 360 may comprise an energy transfer surface 364 of an ultrasonic bonding device 366. As such, the bonding device 366 may include a horn 368 and may be configured to impart ultrasonic energy to the elastic laminate 200 on the combining roll 306. It is to be appreciated that aspects of the ultrasonic bonding device 366 may be configured in various ways, such as for example linear or rotary type configurations, and such as disclosed for example in U.S. Pat. Nos. 3,113,225; 3,562,041; 3,733,238;

5,110,403; 6,036,796; 6,508,641; and 6,645,330, all of which are incorporated by reference herein. In some configurations, the ultrasonic bonding device 366 may be configured as a linear oscillating type sonotrode, such as for example, available from Herrmann Ultrasonic, Inc. In some configurations, the sonotrode may include a plurality of sonotrodes nested together in the cross direction CD.

It is to be appreciated that the bonding device 358 may be configured in various ways, such as with heated or unheated pattern rolls, anvil rolls and/or ultrasonic bonding devices. In some configurations, the pressing surface 360 may be configured as an outer circumferential surface of an anvil roll. Thus, as the elastic laminate 200 advances through the nip 362, the first and second substrates 202, 204 may be mechanically bonded or welded together with pressure exerted between the pressing surface 360 and the outer circumferential surface 308 of the combining roll 306. It is to be appreciated that the combining roll 306 and/or pressing surface 360 may be configured to apply heat and pressure in various ways to perform mechanical bonding, such as for example, the mechanical bonding devices and methods disclosed in in U.S. Pat. Nos. 4,854,984; 6,248,195; 8,778,127; 9,005,392; 9,962,297; and 10,052,237, all of which are incorporated by reference herein. It is also to be appreciated that the combining roll 306 may be configured as an anvil roll and the pressing surface 360 may be defined by the outer circumferential surface of a pattern roll.

In yet other configurations, the apparatus 300 may be configured with one or more adhesive applicator devices adapted to apply adhesive to the second surface 220 of the first substrate 202 and/or the first surface 226 of the second substrate 204, wherein the first and second substrates 202, 204 are bonded together with the applied adhesive in the bond regions 203. It is to be appreciated that such adhesive applicator devices may be configured in various ways, such as for example, as a spray nozzle and/or a slot coating device. In some configurations, the adhesive applicator device may be configured in accordance with the apparatuses and/or methods disclosed in U.S. Pat. Nos. 8,186,296; 9,265,672; 9,248,054; and 9,295,590 and U.S. Patent Publication No. 2014/0148773 A1, which are all incorporated by reference herein. It is also to be appreciated that adhesive may be applied to create the bond regions 230 in conjunction with or instead of the mechanical bonding processes discussed above.

Figure 11A:
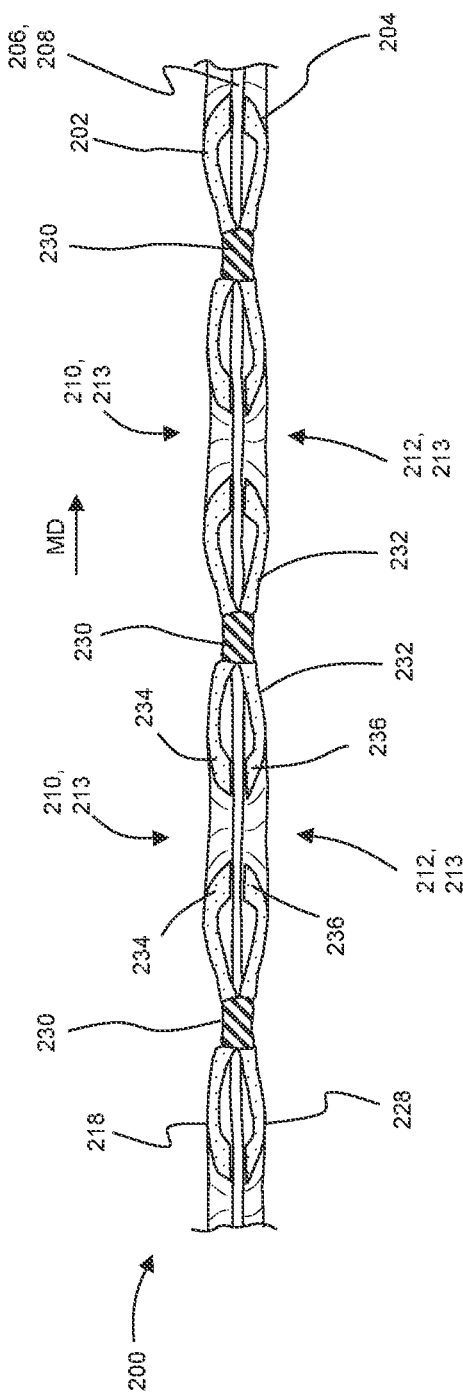
FIG. 11A is a view of the elastic laminate taken along section 11A-11A in FIG. 11.
Figure 12A:
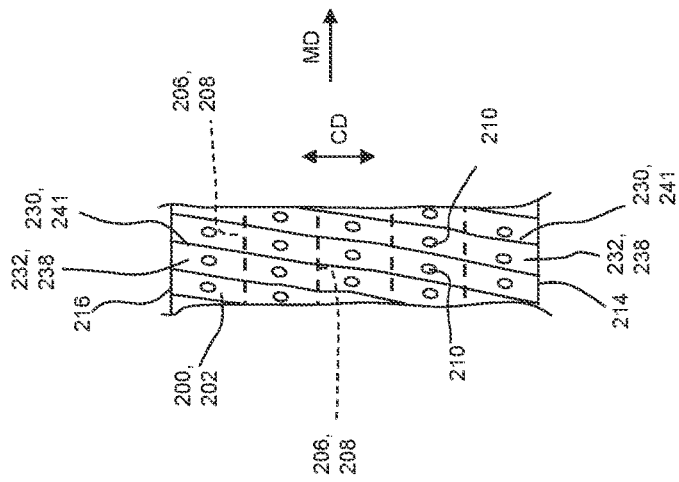
FIG. 12A is a view of an elastic laminate in a relaxed or contracted state with corrugation lines that are not substantially perpendicular to the machine direction.
Figure 12:
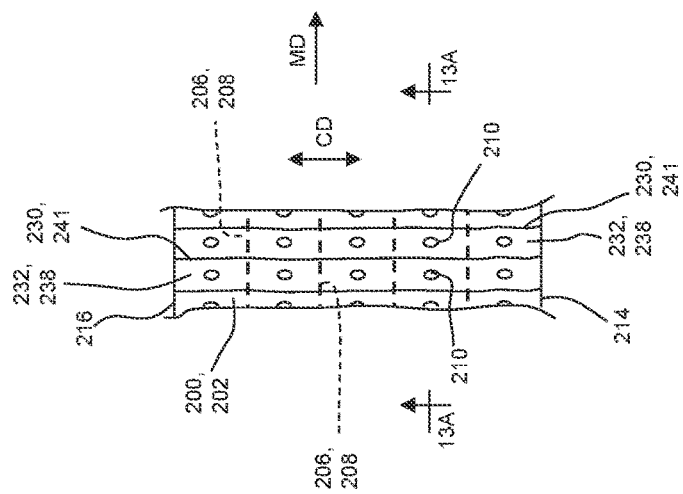
FIG. 12 is a view of the elastic laminate of FIG. 11 in a relaxed or contracted state.
Figure 13B:
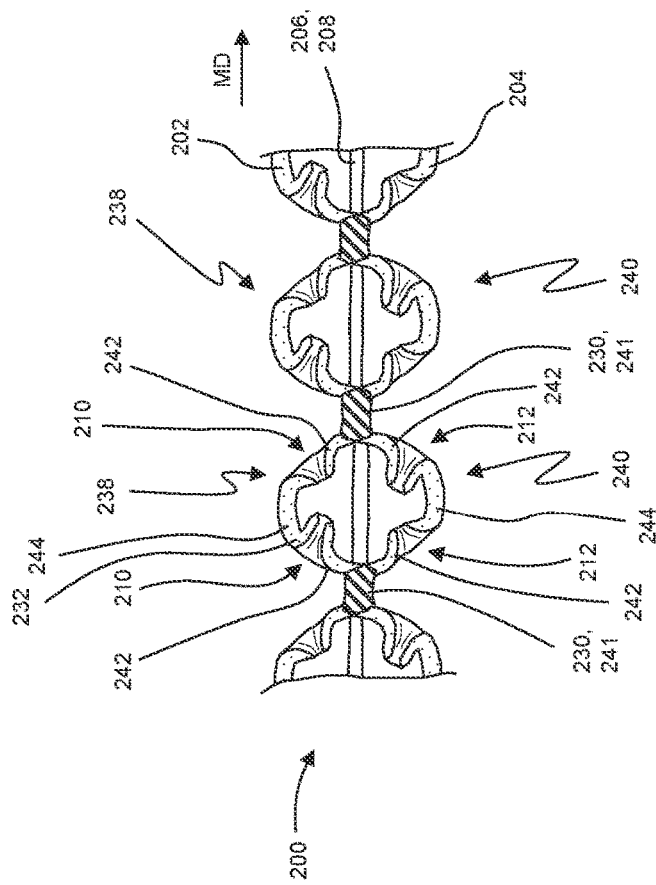
FIG. 13B is a cross sectional view of an elastic laminate in a relaxed state with apertures positioned in sides of corrugations.
Figure 13A:
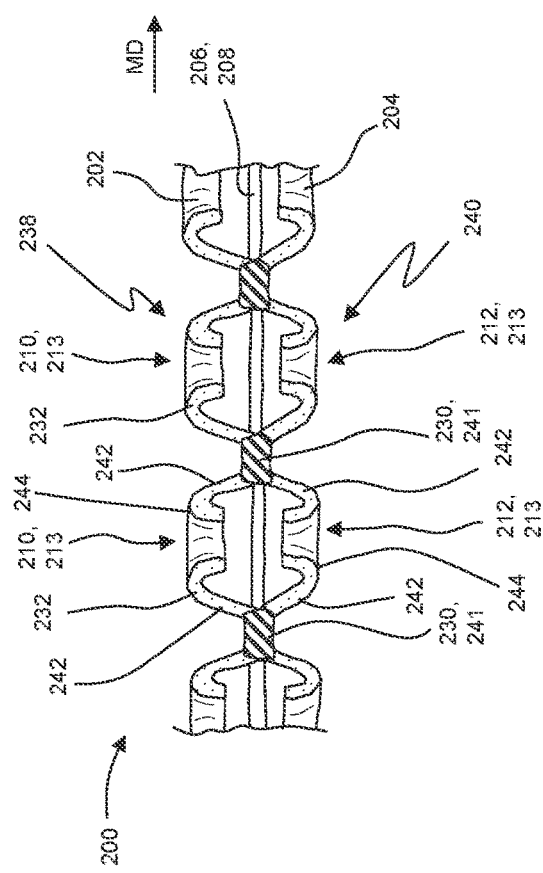
FIG. 13A is a cross sectional view of the elastic laminate in a relaxed state with apertures positioned in peaks of corrugations taken along section 13A-13A in FIG. 12.

With continued reference to FIGS. 4A, 11A, 12, and 13A, after the bond regions 230 are created, tension may be removed from the elastic laminate 200, which in turn allows the elastic strands 208 to contract in the machine direction MD. In turn, first corrugations 238 are formed in the first substrate 202 and second corrugations 240 are formed in the second substrate 204. As shown in FIGS. 12 and 13A, the first corrugations 238 and second corrugations 240 are positioned in unbonded regions 232 between the bond regions 230. The first corrugations 238 and second corrugations 240 extend outward from the bond regions 230 in opposite directions, wherein the first corrugations 238 and second corrugations 240 each include walls 242 extending from the bond regions 230 to a peak 244. The bond regions 230 may also define corrugation lines 241 in the elastic laminate 200 that extend in the cross direction CD between the first corrugations 238 and second corrugations 240.

As discussed above with particular reference to FIGS. 4A, 10A, and 11A, the arrangement of the various elements of the first aperturing device 302 and the second aperturing device 304 and the combining roll 306 may help to provide the ability to assemble elastic laminates 200 with the first protuberances 234 on the first substrate 202 and the second protuberances 236 on the second substrate 204 to be oriented so as to extend toward each other. In contrast to having the protuberances 234, 236 extending outward from the elastic laminate 200, assembling the elastic laminate 200 with the protuberances 234, 236 extending inward or internally of the elastic laminate 200 may help reduce roughness and/or rough feeling that may otherwise be caused by the aperturing processes. As such, it is to be appreciated that the apparatus 300 herein may be configured in various different ways to assemble elastic laminates 200 with the internally extending/oriented protuberances 234, 236.

For example, as shown in FIG. 4B, the first aperturing device 302 includes a first perforator roll 318 adjacent a first anvil roll 320 to define a first aperturing nip 322 therebetween, such as described above. The first aperturing device 302 may also include a transfer roll 370 that may include an outer circumferential surface 372 adapted to rotate about an axis 374 in a direction opposite the first perforator roll 318. The transfer roll 370 may be arranged such that a transfer nip 376 is defined between the transfer roll 370 and the first perforator roll 318. The transfer roll 370 may also be arranged such that the first combining nip 312 is defined between the transfer roll 370 and the combining roll 306, and wherein the transfer roll 370 and the combining roll 306 rotate in opposite directions. In operation, the first substrate 202 may advance in the machine direction MD to the first aperturing device 302 with the first surface 218 of the first substrate 202 in a facing relationship with the outer circumferential surface 324 and pin members 326 of the first perforator roll 318. The first substrate 202 advances through the first aperturing nip 322 where the first pin members 326 penetrate the first substrate 202 and form first apertures 210 in the first substrate 202, such as shown with additional reference to FIGS. 5, 6, and 6A.

As shown in FIG. 4B and as discussed above with reference to FIG. 6B, the first pin members 326 may be directed from the first surface 218 toward the second surface 220 of the first substrate 202. As the first pin members 326 penetrate the first substrate 202, the first pin members 326 may deform the first substrate 202 to define first protuberances 234 extending outward from the second surface 220. With continued reference to FIGS. 4B, 5, and 6, the first substrate may advance on the outer circumferential surface 324 of the first perforator roll 318 from the first aperturing nip 322 and through the transfer nip 376. The first substrate 202 is transferred onto the transfer roll 370 with the second surface 220 of the first substrate 202 in a facing relationship with the outer circumferential surface 372 of the transfer roll 370. As such, the first protuberances 234 extend radially inward toward the outer circumferential surface 372 of the transfer roll 370. In turn, the first substrate 202 may advance on the outer circumferential surface 372 of the transfer roll 370 from the transfer nip 376 and through the first combining nip 312. As such, the first substrate 202 is transferred onto the combining roll 306 with the first surface 218 of the first substrate 202 in a facing relationship with the outer circumferential surface 308 of the combining roll 306. As such, the first protuberances 234 extend radially outward from the combining roll 306. As shown in FIGS. 4B and 9, elastic strands 208 are also advanced in the machine direction MD to the combining roll 306 and onto the second surface 220 of the first substrate 202 as described above.

With continued reference to FIG. 4B, the second aperturing device 304 includes a second perforator roll 334 adjacent a second anvil roll 336 to define a second aperturing nip 338 therebetween, such as described above. The second perforator roll 334 may be arranged such that the second combining nip 314 is defined between the second perforator roll 334 and the combining roll 306, and wherein the second perforator roll 334 and the combining roll 306 rotate in opposite directions. The second substrate 204 may advance in the machine direction MD to the second aperturing device 304 with the second surface 228 of the second substrate 204 in a facing relationship with the outer circumferential surface 340 and second pin members 342 of the second perforator roll 334. The second substrate 204 advances through the second aperturing nip 338 where the second pin members 342 penetrate the second substrate 204 and form second apertures 212 in the second substrate 204.

Figure 10:
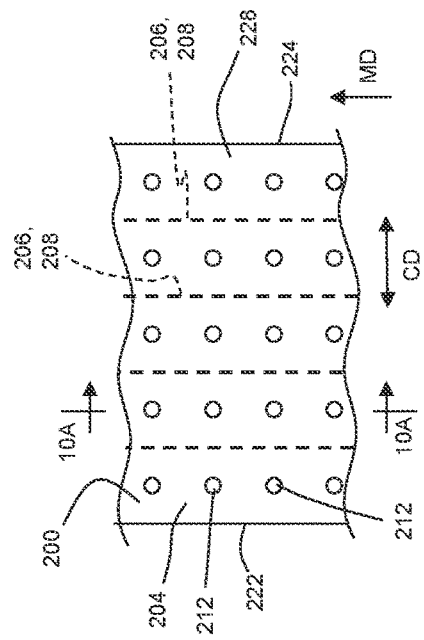
FIG. 10 is a view of an elastic laminate taken along section 10-10 in FIGS. 4A, 4B, and 4C.
Figure 11:
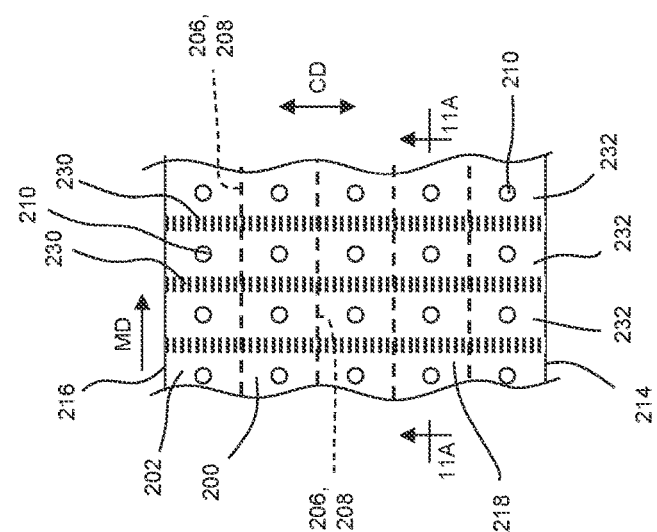
FIG. 11 is a view of the elastic laminate with bond regions taken along section 11-11 in FIGS. 4A, 4B, and 4C.

As shown in FIG. 4B and as discussed above with reference to FIG. 8B, the second pin members 342 may be directed from the second surface 228 toward the first surface 226 of the second substrate 204. As the second pin members 342 penetrate the second substrate 204, the second pin members 342 may deform the second substrate 204 to define second protuberances 236 extending outward from first surface 226. With reference to FIGS. 4B and 10, the second substrate 204 may advance on the outer circumferential surface 340 of the second perforator roll 334 from the second aperturing nip 338 and through the second combining nip 314. As such, the second substrate 204 is transferred onto the combining roll 306 with the first surface 226 of the second substrate 204 in a facing relationship with second surface 220 of the first substrate 202 and stretched elastic strands 208 on the combining roll 306 to form an elastic laminate 200. In addition, the second protuberances 236 extend radially inward toward the outer circumferential surface 308 of the combining roll 306. Thus, as shown in FIGS. 4B, 10, 10A, 11, and 11A, the elastic laminate 200 may be assembled such that the first protuberances 234 on the first substrate 202 extend toward the second substrate 204, and the second protuberances 236 on the second substrate 204 extend toward the first substrate 202.

In another example, such as shown in FIG. 4C, the first aperturing device 302 may be configured in the same manner as the first aperturing device 302 described above with reference to FIG. 4A. Thus, the first substrate 202 may advance on the outer circumferential surface 330 of the first anvil roll 320 from the first aperturing nip 322 and through the first combining nip 312. As such, the first substrate 202 is transferred onto the combining roll 306 with the first surface 218 of the first substrate 202 in a facing relationship with the outer circumferential surface 308 of the combining roll 306. In addition, the first protuberances 234 extend radially outward from the combining roll 306. Elastic strands 208 are also advanced in the machine direction MD to the combining roll 306 and onto the second surface 220 of the first substrate 202 as shown in FIG. 4C and as described above with reference to FIG. 9. In addition, the second aperturing device 304 in FIG. 4C may be configured in the same manner as the second aperturing device 304 described above with reference to FIG. 4B. Thus, the second substrate 204 may advance on the outer circumferential surface 340 of the second perforator roll 334 from the second aperturing nip 338 and through the second combining nip 314. With reference to FIGS. 4C and 10, the second substrate 204 is transferred onto the combining roll 306 with the first surface 226 of the second substrate 204 in a facing relationship with second surface 220 of the first substrate 202 and stretched elastic strands 208 on the combining roll 306 to form an elastic laminate 200. In addition, the second protuberances 236 extend radially inward toward the outer circumferential surface 308 of the combining roll 306. Again, as shown in FIGS. 4C, 10, 10A, 11, and 11A, the elastic laminate 200 may be assembled such that the first protuberances 234 on the first substrate 202 extend toward the second substrate 204, and the second protuberances 236 on the second substrate 204 extend toward the first substrate 202.

It is also to be appreciated that the apparatuses shown in FIGS. 4A-4C may include additional anvil rolls and/or perforator rolls. In some configurations, the transfer rolls described above may also be adapted to function as anvil rolls. In addition, the aperturing devices, anvil rolls, and/or perforator rolls herein may be constructed in various ways and/or operate in various ways, such as disclosed for example, in U.S. Pat. No. 4,886,632 and U.S. Patent Publication Nos. 2018/0228666 A1; 2018/0228656 A1; and 2018/0228668 A1, all of which are incorporated by reference herein.

Although the various elements of the first aperturing device 302 and the second aperturing device 304 and the combining roll 306 may be configured to assemble elastic laminates 200 with the first protuberances 234 on the first substrate 202 and the second protuberances 236 on the second substrate 204 to be oriented so as to extend toward each other, it is also to be appreciated that the apparatuses herein may also be configured to assemble elastic laminates 200 with one substrate having outwardly extending/oriented protuberances and one substrate with internally/oriented protuberances. For example, the elastic laminate 200 may include a first substrate 202 with first protuberances 234 that extend outward and away from the second substrate 204, and a second substrate 204 with second protuberances 236 that extend inward and toward the first substrate 202. In addition, the apparatuses herein may also be configured to assemble elastic laminates 200 with both substrates having outwardly extending/oriented protuberances. For example, the elastic laminate 200 may include a first substrate 202 with first protuberances 234 that extend outward and away from the second substrate 204 and a second substrate 204 with second protuberances 236 that extend outward and away from the first substrate 202.

Figure 10A:
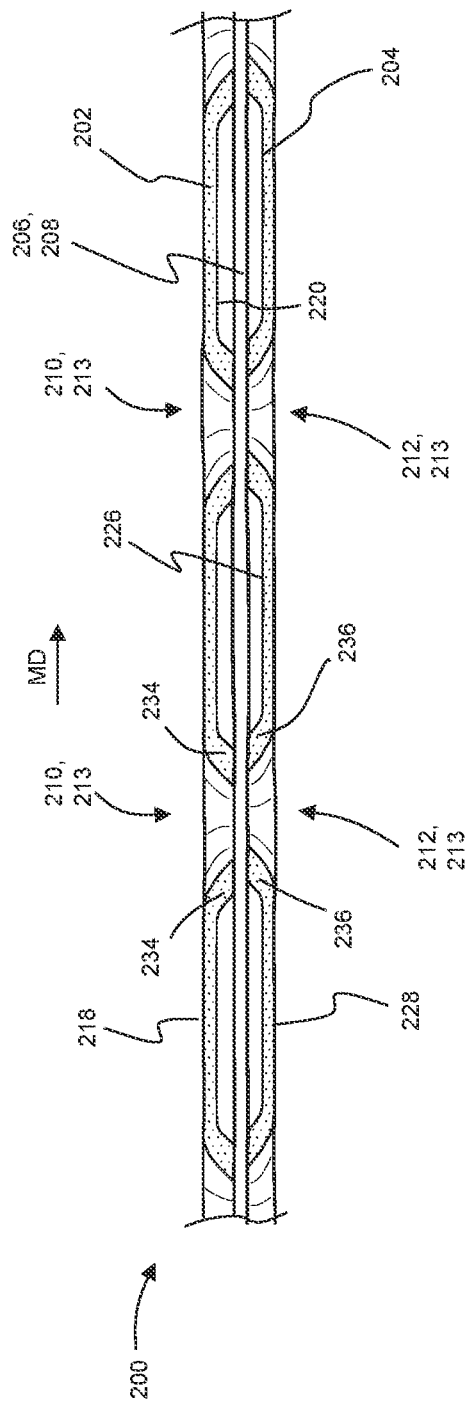
FIG. 10A is a view of the elastic laminate taken along section 10A-10A in FIG. 10.

As previously mentioned, the close coupled arrangement of the aperturing devices 302, 304 and the combining roll 306 help provide the ability to more precisely control the registration and/or positions and/or placement of the apertures 210, 212 in the assembled laminate 200 relative to each other. For example, as shown FIGS. 11 and 11A, the first substrate 202 and the second substrate 204 are bonded together in bond regions 230, wherein the bond regions 230 are separated from each other along the machine direction MD to define unbonded regions 232. The first apertures 210 and the second apertures 212 may be positioned in the unbonded regions 232. In some configurations, such as shown in FIGS. 10A, 11A, and 13A, the first apertures 210 and the second apertures 212 may be aligned to define apertures 213 that extend completely through the elastic laminate 200. As such, it is to be appreciated that the first apertures 210 and the second apertures 212 may be aligned so as to have substantially coterminous outer circumferences wherein the apertures 213 are shaped similar to the first and second apertures 210, 212. In some configurations, the first and second apertures 210, 212 may have different shapes and/or may be aligned to partially overlap each other to define apertures 213 having various different shapes and/or sizes. In some configurations, such as shown in FIG. 13A, the first apertures 210 may be positioned on the peaks 244 of the first corrugations 238 and/or the second apertures 212 may be positioned on the peaks 244 of the second corrugations 240. In some configurations, such as shown in FIG. 13B, the first apertures 210 may be positioned on the walls 242 of the first corrugations 238 and/or the second apertures 212 may be positioned on the walls 242 of the second corrugations 240. In some configurations, some first apertures 210 may be positioned on the peaks 244 of the first corrugations 238 and some first apertures 210 may be positioned on the walls 242 of the first corrugations 238 and/or some second apertures 212 may be positioned on the peaks 244 of the second corrugations 240 and some second apertures 212 may be positioned on the walls 242 of the second corrugations 240. It is also to be appreciated that a plurality of first apertures 210 and/or second apertures 212 may be positioned between the bond regions 230. For example, FIG. 13B shows two first apertures 210 and two second apertures 212 positioned between the bond regions 230 and positioned in the unbonded regions 232.

The close coupled arrangement of the aperturing devices 302, 304 and the combining roll 306 also help provide the ability to more precisely control the registration and/or positions and/or placement of the apertures 210, 212 in the assembled laminate 200 relative to the bond regions 230 and corrugation lines 241 that may be defined thereby. For example, as shown in FIG. 12, the bond regions 230 and resulting corrugation lines 241 may be oriented to extend in a direction that is substantially perpendicular with respect to the machine direction MD. As such, the aperturing devices 302, 304 and the combining roll 306 arrangements herein help control the registration and/or positions and/or placement of the apertures 210, 212 along the machine direction MD in the assembled laminate 200 relative to the bond regions 230 and corrugation lines 241. It is also to be appreciated that bonding equipment configurations may be adapted to create bond regions 230 and/or resulting corrugation lines 241 that are not substantially perpendicular with respect to the machine direction MD such as shown in FIG. 12A and/or may extend in the cross direction CD in wavy or curved lines. In turn, it is to be appreciated that the aperturing devices 302, 304 and the combining roll 306 arrangements herein help control the registration and/or positions and/or placement of the apertures 210, 212 along the machine direction MD as well as the cross direction CD in the assembled laminate 200 relative to the bond regions 230 and corrugation lines 241.

Figure 14:
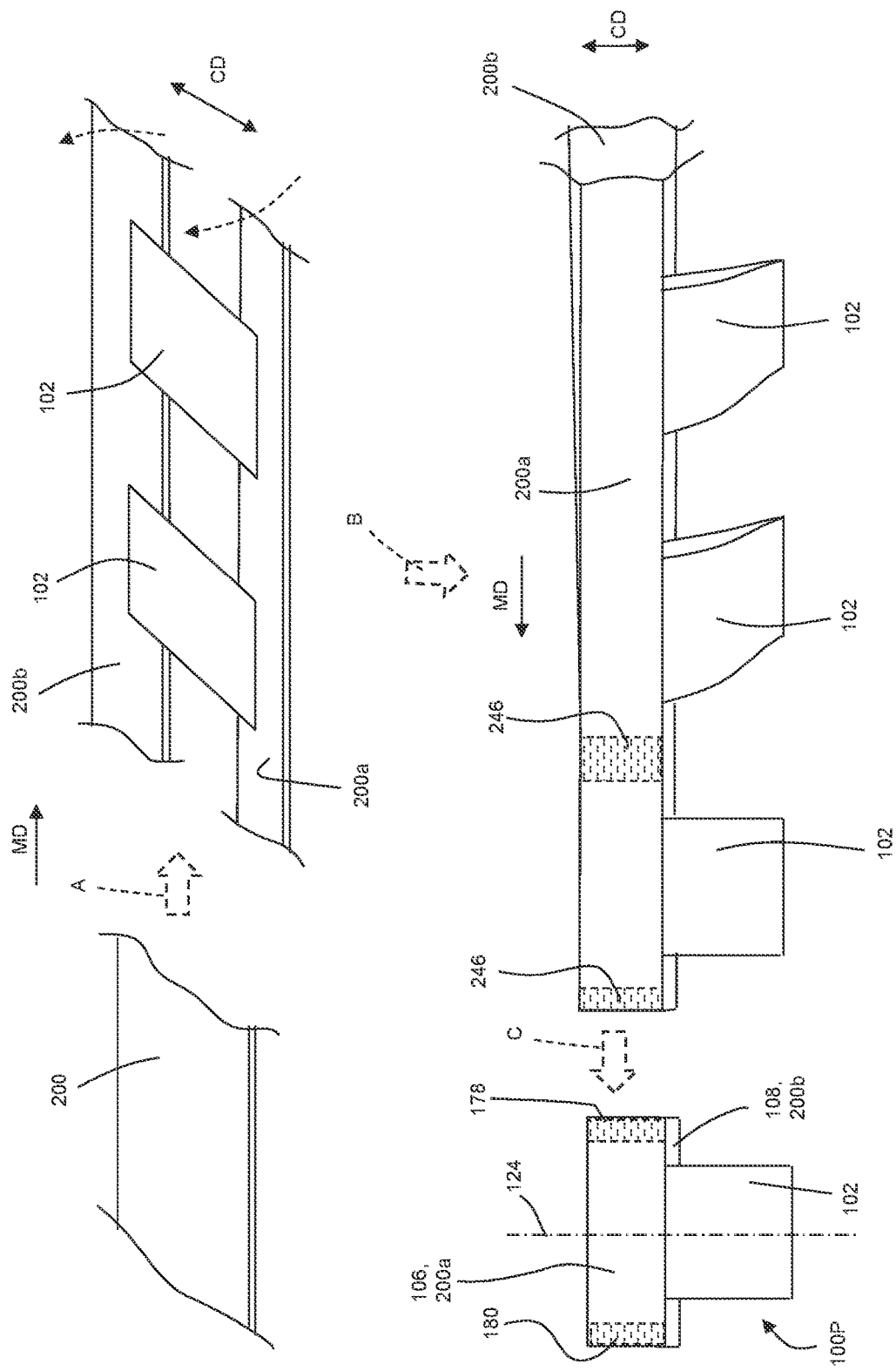
FIG. 14 is a schematic view of a diaper pant assembly process.

As described above, it is to be appreciated that the elastic laminates 200 herein can be used to construct various types of absorbent article components. For example, the elastic laminates 200 may be used as a continuous length of elastomeric belt material that may be converted into the first and second elastic belts 106, 108 discussed above with reference to FIGS. 1-3B. As such, the elastic material 206 may correspond with the belt elastic material 168 interposed between the outer layer 162 and the inner layer 164, which in turn, may correspond with either the first and/or second substrates 202, 204. For example, as shown in FIG. 14, when assembling diaper pants 100P, the elastic laminate 200 may be converted into a first elastic belt laminate 200a and/or a second elastic belt laminate 200b (represented by the dashed arrow "A"). The first elastic belt laminate 200a and the second elastic belt laminate 200b may be separated from each other in the cross direction CD and may be connected with each other with a plurality of chassis 102 intermittently spaced along the machine direction MD. During subsequent assembly operations, the chassis 102 may be folded (represented by the dashed arrow "B") so as to position the first elastic belt laminate 200a into a facing relationship with the second elastic belt laminate 200b. Bonds 246 may be applied to the overlapping belt laminates 200a, 200b. Subsequently, discrete diaper pants 100P may be formed by separating the first and second belt laminates 200a, 200b into first and second belts 106, 108 by cutting along the cross direction CD through the first and second belt laminates 200a, 200b adjacent the bonds 246 (represented by the dashed arrow "C"). As such, the bonds 246 may be divided to define the first and second side seams 178, 180, respectively.

With further regard to incorporating the elastic laminates 200 herein into various diaper assembly processes, it is also to be appreciated that the bond regions 230 discussed herein with reference to the accompanying figures may be configured in various ways. For example, the bond regions 230, may be configured as anchoring bonds and trapping bonds or guiding bonds. More particularly, the anchoring bonds may be configured to anchor and bond discrete lengths of the stretched elastic strands 208 with and between the first substrate 202 and the second substrate 204, and trapping bonds may be configured to bond the first and second substrates 202, 204 directly to each other, wherein the trapping bonds may be separated from each other in a cross direction by at least one elastic strand 208, and as such, the elastic strands 208 may be trapped between the trapping bonds. In some configurations, the trapping bonds may be arranged to bond the first and second substrates 202, 204 directly together without adhering the elastic strands 208 to either substrate. As such, the trapping bonds may be configured to trap and immobilize discrete lengths of the elastic strands 208 between the trapping bonds after the elastic strands 208 have contracted, such as disclosed for example, in U.S. Pat. No. 6,291,039 and U.S. Patent Publication Nos. 2016/0331600 A1; 2018/0168880 A1; 2018/0170027 A1; and 2018/0168879 A1, all of which are incorporated by reference herein.

It is also to be appreciated that the elastic laminates 200 herein may be configured to be subjected to various elastic strand cutting processes, sometimes referred to as tummy elastic cutting, to create deactivated regions in the elastic laminate positioned along the machine direction between elasticized regions by severing at least one stretched elastic strand, wherein the at least one severed elastic strand retracts to at least one anchor bond. In some assembly operations, absorbent chassis 102 may be connected with the elastic laminate 200 in such deactivated regions. As such, it also to be appreciated that the methods and apparatuses herein may be adapted to operate with various types of absorbent article assembly processes that may incorporate elastic laminates assembled thereby, such as disclosed for example in U.S. Pat. Nos. 8,186,296; 9,265,672; 9,248,054; and 9,730,839 and U.S. Patent Publication Nos. 2013/0255861 A1; 2013/0255862 A1; 2013/0255863 A1; 2013/0255864 A1; 2013/0255865 A1; 2018/0169964 A1; and 2018/0168879 A1, all of which are incorporated by reference herein. In other examples, the elastic laminates 200 herein may be used to construct various types of leg cuff, backsheet, and/or topsheet configurations. In yet other examples, the elastic laminates may be used to construct waistbands and/or side panels in taped diaper configurations.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
    an elastic laminate comprising:
        a first substrate comprising a first surface and an opposing second surface, and first apertures surrounded by first protuberances extending outward from second surface;
        a second substrate comprising a first surface and an opposing second surface, and second apertures surrounded by second protuberances extending outward from the first surface;
        elastic strands positioned between the first and second substrates;
        the first substrate bonded with the second substrate in bond regions, wherein the second surface of the first substrate is in a facing relationship with the first surface of the second substrate, and wherein the bond regions are separated from each other by unbonded regions, and wherein the first protuberances and the second protuberances are positioned entirely in the unbonded regions; and
    an absorbent chassis connected with the elastic laminate.

2. The absorbent article of claim 1, the elastic laminate further comprising:
    first corrugations in the first substrate; and
    second corrugations in the second substrate;
    wherein the first and second corrugations are positioned between the bond regions; and
    wherein the first and second corrugations each include walls extending from the bond regions to a peak.

3. The absorbent article of claim 2, wherein the first apertures are positioned on the peaks or walls of the first corrugations.

4. The absorbent article of claim 3, wherein the first apertures and the second apertures are aligned to define apertures that extend through the elastic laminate.

5. The absorbent article of claim 1, wherein the first protuberances comprise substantially frustoconical shaped sides.

* * * * *